(12) United States Patent
Schaff et al.

(10) Patent No.: US 10,870,109 B2
(45) Date of Patent: Dec. 22, 2020

(54) SAMPLE CUP

(71) Applicant: Sandstone Diagnostics, Inc., Pleasanton, CA (US)

(72) Inventors: Ulrich Schaff, Livermore, CA (US); Jon Epperson, Livermore, CA (US); Laura Fredriksen, Berkeley, CA (US); Kirk Harmon, San Ramon, CA (US)

(73) Assignee: Sandstone Diagnostics, Inc., Pleasanton, CA (US)

( * ) Notice: Subject to any disclaimer, the term of this patent is extended or adjusted under 35 U.S.C. 154(b) by 0 days.

(21) Appl. No.: 16/480,284

(22) PCT Filed: May 20, 2017

(86) PCT No.: PCT/US2017/033710
§ 371 (c)(1),
(2) Date: Jul. 23, 2019

(87) PCT Pub. No.: WO2018/217184
PCT Pub. Date: Nov. 29, 2018

(65) Prior Publication Data
US 2020/0030789 A1  Jan. 30, 2020

(51) Int. Cl.
*B01L 3/00* (2006.01)
*A61B 10/00* (2006.01)
(Continued)

(52) U.S. Cl.
CPC .......... *B01L 3/502* (2013.01); *A61B 10/0058* (2013.01); *G01F 19/00* (2013.01);
(Continued)

(58) Field of Classification Search
CPC . B01L 3/502; B01L 2400/0457; G01N 21/07; G01N 2021/0357; G01N 2021/0378; G01N 2035/0401
See application file for complete search history.

(56) References Cited

U.S. PATENT DOCUMENTS 2,569,702 A  10/1951  Warner
3,401,696 A   9/1968  O'Brien
(Continued)

FOREIGN PATENT DOCUMENTS

EP  0 173 811 A1  1/1985
GB     2162312 A  1/1986
(Continued)

*Primary Examiner* — Jill A Warden
*Assistant Examiner* — Dwayne K Handy
(74) *Attorney, Agent, or Firm* — Kim Rubin (57) ABSTRACT

A cup used to receive, hold, measure and pour liquids, such a specimens, such as for a medical assay, is described. The cup comprises an open receiving upper chamber, two or more open sample-directing channels, and an open, calibrated and marked measuring column. When sitting on a level surface, fluid flows freely from the upper chamber through the sample-directing channels into the measuring column. A foot is under each fluid-directing channel. The base of the measuring column functions as an additional, such as a third, foot. Cups nest, with the two feet of the upper cup sitting into two sample-directing columns of lower cup. The measuring column and upper chamber taper to permit nesting. If the cup is tipped, it rests on two of three of: the two feet and the base of the measuring column, and a point on a lower perimeter of the upper chamber, such that fluid will not spill.

16 Claims, 5 Drawing Sheets

(51) Int. Cl.
 *G01F 19/00* (2006.01)
 *G01N 1/20* (2006.01)
(52) U.S. Cl.
 CPC .......... *G01N 1/20* (2013.01); *B01L 2300/028*
   (2013.01); *B01L 2300/087* (2013.01); *B01L*
   *2300/0832* (2013.01); *B01L 2300/0851*
   (2013.01); *B01L 2300/16* (2013.01); *B01L*
   *2400/0457* (2013.01)

(56) References Cited

U.S. PATENT DOCUMENTS

| | | |
|---|---|---|
| 3,518,164 A | 6/1970 | Andelin |
| 4,300,404 A | 11/1981 | Mehl |
| D267,118 S | 11/1982 | Bernett |
| 4,530,816 A | 7/1985 | Douglas-Hamilton |
| 4,799,599 A | 1/1989 | Herrman |
| 5,068,089 A | 11/1991 | Ericssson |
| 5,232,120 A | 8/1993 | Dunken et al. |
| 5,358,690 A | 10/1994 | Guirguis |
| D398,993 S | 9/1998 | Jones |
| 5,807,360 A | 9/1998 | Shubin |
| 6,291,178 B1 | 9/2001 | Schneider |
| 7,077,000 B2 | 7/2006 | Gouldsworthy |
| D558,384 S | 12/2007 | Bickler et al. |
| D560,813 S | 1/2008 | Matusuura |
| D631,558 S | 1/2011 | Harmston |
| 7,864,046 B2 | 1/2011 | Yarsa et al. |
| 7,947,026 B2 | 5/2011 | Herr et al. |
| D641,866 S | 7/2011 | Burgess |
| 7,993,315 B2 | 8/2011 | Matusuura |
| D660,451 S | 5/2012 | Matusuura |
| 8,163,253 B1 | 5/2012 | Hartselle |
| 8,353,887 B2 | 1/2013 | Matusuura |
| 8,475,422 B2 | 7/2013 | Wu |
| 8,535,622 B2 | 9/2013 | Shany |
| D739,552 S | 9/2015 | Hoke |
| D762,299 S | 7/2016 | Matusuura |
| 9,594,034 B1 | 3/2017 | Pompa |
| 2005/0011261 A1 | 1/2005 | Lyon |
| 2005/0058163 A1 | 3/2005 | Kane et al. |
| 2007/0031895 A1 | 2/2007 | Herr |
| 2011/0084070 A1 | 4/2011 | Martheenal |
| 2012/0164751 A1 | 6/2012 | Liang et al. |
| 2016/0320276 A9 | 11/2016 | Schaff et al. |

FOREIGN PATENT DOCUMENTS

| | | |
|---|---|---|
| WO | WO 2011/110469 A1 | 9/2011 |
| WO | WO2011/110469 A1 | 9/2011 |
| WO | WO2014/191207 A1 | 12/2014 |
| WO | WO20161884430 A1 | 12/2016 |

SAMPLE CUP

This invention claims priority and benefit to to PCT application PCT/US17/33710, filed 20 May 2017.

TECHNICAL FIELD

This invention relates generally to receiving, holding and measuring fluids. More specifically, the invention relates to a cup for this purpose.

BACKGROUND OF THE INVENTION

Prior art in this field includes: Cawood GB2162312A; Oastane US20050059163A1; Douglas-Hamilton U.S. Pat. No. 4,530,816; Eisenson U.S. Pat. No. 6,426,213; Ericsson U.S. Pat. No. 5,068,089; Glefand U.S. Pat. No. 9,517,026; Gouldsworthy U.S. Pat. No. 7,077,000; Guirguis U.S. Pat. No. 5,358,690; Harmston U.S. D631558; Herr US20070031895; Herrmann U.S. Pat. No. 4,799,599; Li WO2016188430A1; Matsuura U.S. Pat. No. 7,993,315; Matsuura U.S. Pat. No. 8,353,887; Mehl U.S. Pat. No. 4,300,404; O'Brien U.S. Pat. No. 3,401,696; Pompa U.S. Pat. No. 9,594,034; Prien U.S. Pat. No. 6,864,046; Schneider U.S. Pat. No. 6,291,178; Shany U.S. Pat. No. 8,535,622; Shubin U.S. Pat. No. 5,807,360; Tatneii_ WO2014191207A1; Wang U.S. Pat. No. 0,559,364; Williams 0173811A1; and Wu U.S. Pat. No. 8,475,422.

For some applications, such as collecting and then measuring a quantity of fluid, such as for a biological assay, it is convenient to have a large receiving opening or chamber in a cup or container. However, often the measuring volume is small, such as a milliliter (mL) or less. For such a small volume, a small graduated or ruled container or column is appropriate, which may be much lower volume and a smaller diameter that the receiving chamber. While a funnel could be used, or fluid could be transferred from the initial receiving container to a measurement container, the process requires extra steps and extra equipment, compared to having a single container adapted to both conveniently receive and then conveniently measure a small volume of fluid. Transferring the fluid may cause some fluid to be lost, such as stuck to the side of a container, or spill.

It is desirable that such a container be monolithic and stand stably on its own without requiring a stand or support. It is also desirable to have a container that does not spill if tipped or placed on its side. It is also desirable to have such containers nest for convenience in storing and shipping. Prior art containers do not have simultaneously all such desirable characteristics.

SUMMARY OF THE INVENTION

Embodiments of this invention comprise a cup with a relatively large, open upper (or receiving) chamber which then drains into two recessed sample-directing channels (also referred to as chambers), which in turn drain into a smaller measurement chamber (also referred to as a column). The upper chamber and the channels are tapered such that any fluid in the cup will drain into the measurement chamber, until the measurement chamber is full or overflows back into the channels, without tipping or other movement of the cup.

The two channels have beneath them each a foot. The measurement column has a base. The bottom of the two feet and the base of the measurement column are coplanar so the cup rests upright on these three supports when placed on a horizontal surface.

Some embodiments have a preferred fluid volume. Such a volume may be marked on the measurement column, such as with a distinct line. This marking may be in addition to a scale. This preferred fluid volume may be a minimum volume necessary for an assay of the fluid.

The shape of the cup is such that if placed on its side it then rolls such that three points again support it. These three points are: a point on the lower perimeter of the upper chamber, and two out of three of: the two feet and the base of the measurement column. When so tipped, any fluid of volume equal to or less than a preferred volume will not spill.

Such a cup is well adapted for use by an unskilled individual and for the handling of high-value fluids where a spill is particularly undesirable. Such an individual may be providing a biological sample liquid in the cup.

The upper chamber, sample-directing channels and measurement chamber are tapered such that multiple cups nest. Feet of an upper cup nest into sample-directing channels of a lower cup; while the measuring chambers nest due to their taper.

The cup may have graduations or a scale on the measurement chamber. It may have a pouring spout. It may be coated on the inside with a chemical, such as an enzyme. It may have a receptacle location adapted to hold a pill or other chemical. It may have a cover.

The cup may be part of kit, such as used for a chemical assay. The cup may be used for non-fluids, such as powders or solids in discreet units.

DETAILED DESCRIPTION OF THE INVENTION

All Figures and descriptions are non-limiting embodiments and exemplary scenarios.

Figure 6:
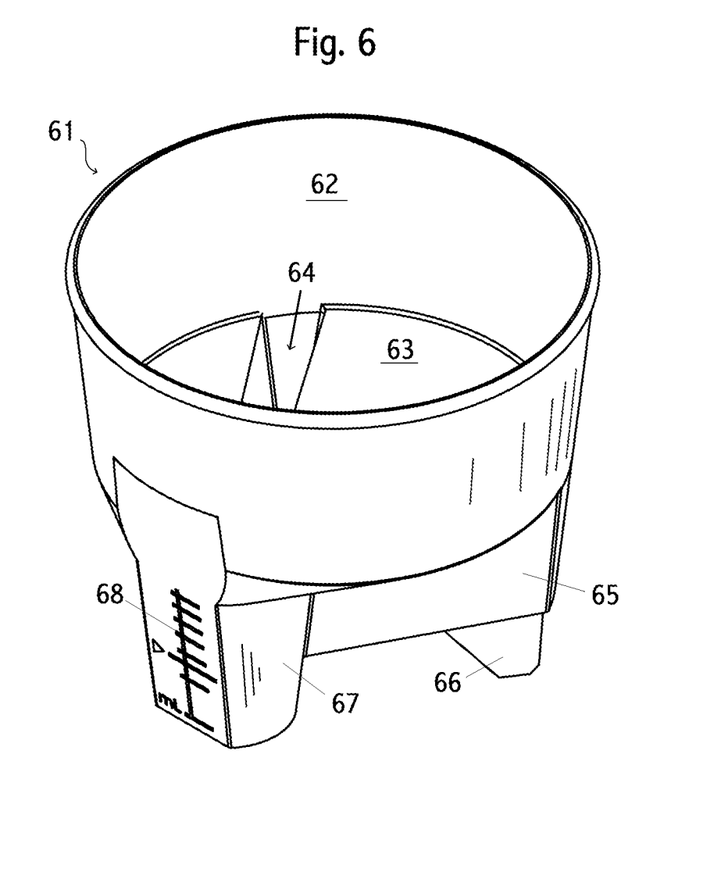
FIG. 6 is a perspective view of an exemplary cup.

Turning first to FIG. 6 we see a view of an exemplary cup 61. 62 is a sidewall of the curved upper chamber, generally in the shape of a tapered cylinder. 63 is the base of the upper chamber, tapered towards both two sample-directing channels 64 and 65, and to the measuring chamber 67. 64 shows how the top of the sample-directing channels are open to the base 63 of the upper chamber so that fluid will drain from the upper chamber into the sample-directing channels or directly into the measuring chamber. 64 shows a view of a first sample-directing channel from the inside of the cup and 65 shows a second sample-directing channel from the outside of the cup. 66 is a foot on the bottom of the second sample-directing channel 65. A similar foot under the first sample-directing channel 64 is not visible. One can see in the Figure that the cup as a whole is tapered, and that the two sample-directing channels are individually tapered, as is the measuring chamber 67. The sample-directing chambers, such as 65, in this embodiment, do not go all the way to the bottom of the cup. In other embodiments, the end of the sample-directing chambers where they meet and are open to the measuring chamber 67 may be at the bottom of the cup. However, the channel should still be tapered towards the measuring chamber 67. Note that for some fluid volumes, a portion of the fluid may be in the measuring chamber and a portion also in one or both sample-directing channels. The scale, 68, provides a reading of fluid volumes without tilting or tipping the cup. The scale 68, in this Figure, has an arrow or other single marking indicating a preferred or predetermined fluid volume. Such a predetermined volume, for semen, may be 1.5 milliliters (mL). Fluid placed in the upper chamber will flow into the measuring chamber without any movement of the cup, such as tilting.

FIG. 6 shows an embodiment where the top rim of the cup—the top of the upper chamber—is circular. Other embodiments are claimed, such as an elliptical, oval, or rounded-corner rectangular or square shape. In one embodiment, shown in this Figure, the cup fits within a minimum diameter circular cylinder that proximally encloses the top rim. The upper rim of the cup may have the same diameter or other dimension(s) of such an enclosing cylinder. In such case, in a downward projection of the cup toward a horizontal surface, no portion of the cup will extend beyond the projection of the upper rim.

Figure 1:
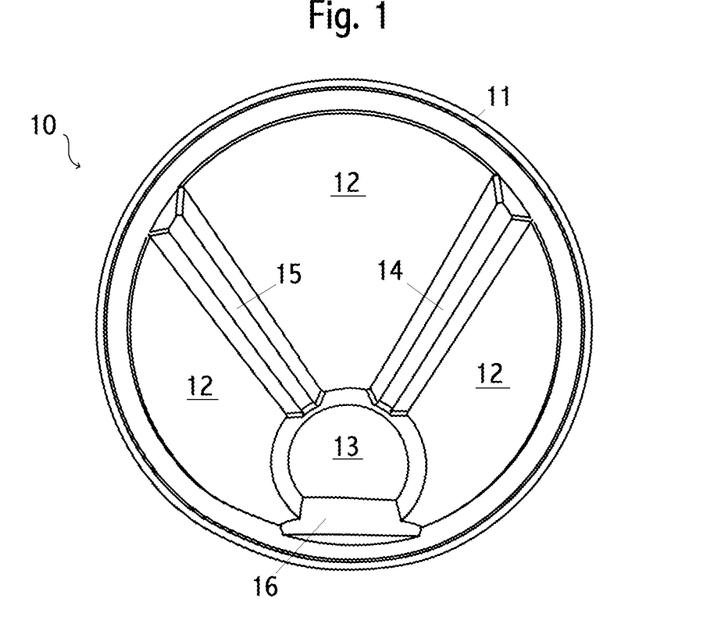
FIG. 1 is a top view of an exemplary cup.

Turning now to FIG. 1 we see a top view of an embodiment of the cup 10. A lip, or rim of the upper chamber, is shown 11. 12 identifies three portions of the base of the upper chamber that are tapered towards the two sample-directing channels 14 and 15 and towards the measuring chamber 13. Careful observation of this Figure reveals the tapered sides of the upper chamber, the sample-directing channels 14 and 15, and the measuring chamber 13. 16 shows a base or foot of the measuring chamber. The measuring chamber may have a wall, that is a portion of the outside of the cup or proximal to the outside of the cup, that is flat. Such a flat provides an easy-to-read graduation, scale or ruler, such as 27 in FIG. 2.

Figure 2:
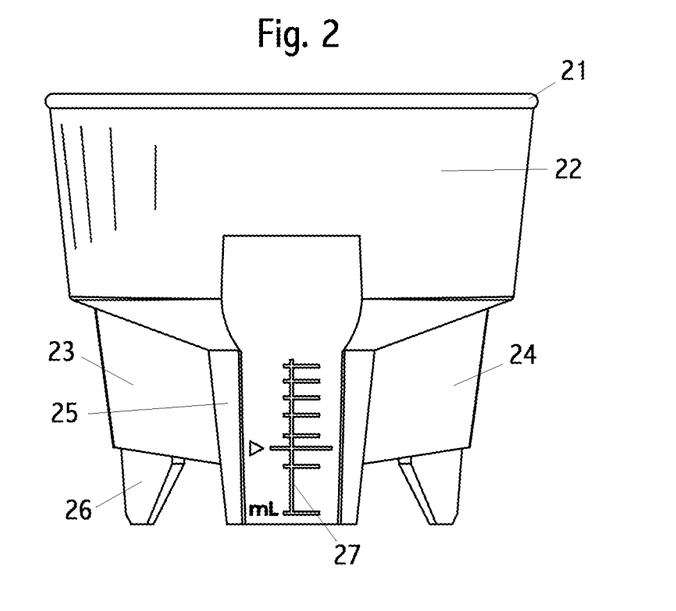
FIG. 2 is a front view of an exemplary cup.

Turning now to FIG. 2 we see a front view of a cup, with the graduation, ruler or scale 27 visible on the side of the measuring chamber 25. A single mark or enhanced line shows a preferred volume, which may be a minimum volume necessary for an assay of the fluid contents of the cup. 21 is the rim of the cup at the top of the upper chamber 22. 23 and 24 identify the sample-directing channels. 26 identifies one of the two feet or bases under the sample-directing channels 23 and 24.

Figure 3:
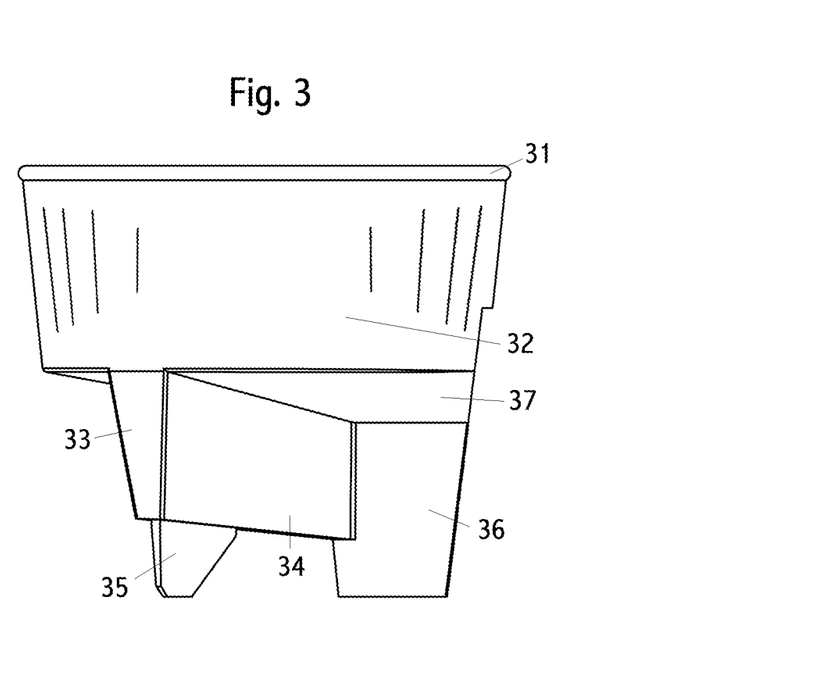
FIG. 3 is a side view of an exemplary cup.

Turning now to FIG. 3, we see a side view of a cup. 31 is the lip of the upper chamber 32. 37 shows a tapered base of the upper chamber 32 leading to a sample-directing channel 33. The bottom of channel 33 is 34, sloped to direct fluid in the channel towards the measuring chamber 36. A foot or base of the sample-directing channel 33 is shown 35. A similar foot of the other sample-directing channel is not visible. Observation of this Figure will show the tapers of the cup as a whole, the upper chamber 32, the sides of the sample-directing channel 33, the base 34 of the sample-directing channel, and measuring chamber 36.

Figure 4:
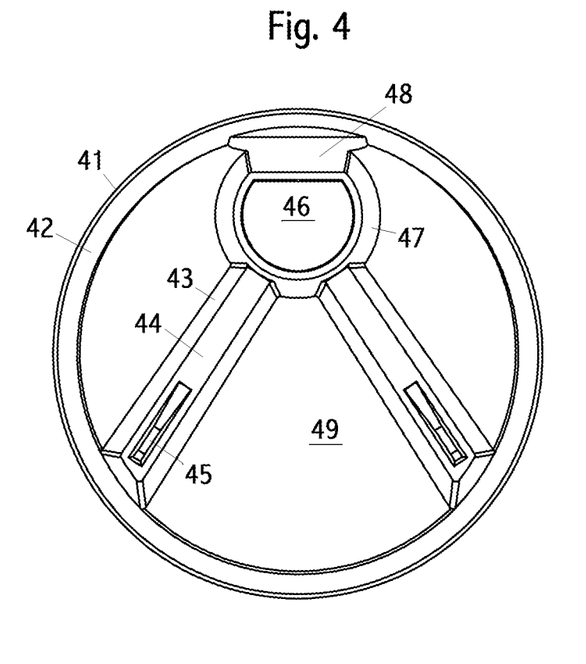
FIG. 4 is a bottom view of an exemplary cup.

Turning now to FIG. 4, we see a bottom view of a cup. This view is important because we can see here easily the three points on which the cup rests upright: the two feet or bases 45 of the sample-directing channels 44, and the bottom of the measuring chamber 46 or a foot or base 48 of the measuring chamber. 41 shows the rim at the top of the upper chamber. 42 shows the tapered side of the upper chamber. 44 shows one of the two sample-directing channels. 43 shows a tapered side of this channel. 49 shows a portion of a sloped base of the upper chamber. 46 shows the bottom of the measuring chamber. 47 shows a tapered side of the measuring chamber.

Figure 5:
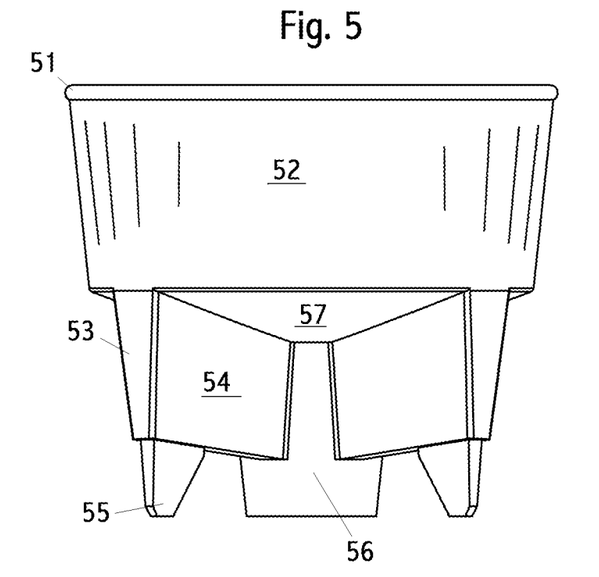
FIG. 5 is a back view of an exemplary cup.

Turning now to FIG. 5, we see a back view of the cup. Here, both sample-directing channels, one identified as 53, are clearly visible. 54 shows a tapered side of one channel. 57 shows a portion of the sloped bottom of the upper chamber 52. 51 is a lip or rim at the top of the upper chamber 52. 55 shows a foot or base under one sample-directing channel 53. 56 shows the back of the measuring chamber.

In some embodiments, one of the resting points may be either the bottom of the measuring chamber or a foot or base connected to the measuring chamber.

Four or more support points may be used in other embodiments. More than two sample-directing channels may be in other embodiments. Although these Figures show sharp-cornered elements or features, any portion of the entire cup may have smooth contours between elements, or be a more organic shape in part or overall. The sample-directing channels may be shallow and may be curved. There may be recesses in the base of the upper chamber.

Figure 7:
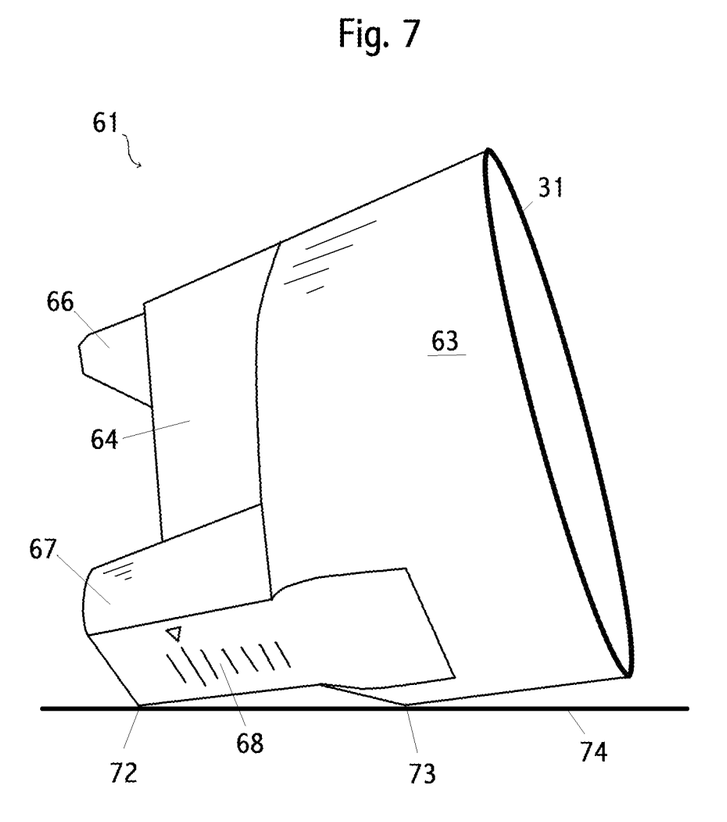
FIG. 7 is a perspective view of an exemplary cup tipped on its side.

Turning now to FIG. 7 we see a cup tipped on its side. Embodiments, when tipped on a level surface, will not spill any liquid up to a predetermined maximum volume, which may be a maximum volume readable on the scale 68, or a desired minimum amount of fluid, such as a marking on the scale, or another volume. On its side, the cup rests on three points: two of three of: the two feet and the measurement chamber, and a point on the lower perimeter of the upper chamber. Reference designators that are the same as in prior Figures are the same element. 61 is the cup as a whole. Cups may be opaque, although transparent or translucent is preferred so that fluid levels are easily viewed. In this Figure, hidden elements are not shown. 66 is one foot. The second foot is not visible. 63 is a wall of the upper chamber. 64 is one sample-directing chamber. The second sample-directing chamber is not visible. 67 is the measuring chamber. 68 is a scale, where a preferred volume triangular mark is visible. 31 is the cup rim. 74 indicates the horizontal surface on which the tipped cup is resting. Two resting points are visible: 72 is a base point on the measuring chamber 67; 73 is a point on the lower perimeter of the upper chamber. The third resting point is the second foot, not visible. A fluid level in the cup is not shown.

Embodiments nest. That is, the upper chambers nest, the sample-directing channels nest, and the measuring chambers nests. In one embodiment the feet or base of the sample-directing channels in the upper cup rest on the bottom of the sample-directing channels in the lower cup. This permits two nested cups to occupy a total height that is no more than 1.3, 1.25, 1.15, 1.10 or 1.05 times the height of a single cup.

Note that a funnel shape with supporting feet will not fully nest. A novelty of embodiments is that the cups nest and are monolithic. In addition, a funnel shape does not have a measuring chamber at the side where it is easily readable.

A summary of features available in one embodiment, not available all at once in the prior art, are: large opening in the upper, or receiving chamber; narrow measurement chamber; tapered so fluid flows without aid to the measurement chamber; three points of support; fully nesting (including measurement chamber); monolithic, easy to read with a graduation scale that is part of or flush with the outside surface of the cup; a single preferred volume indication mark, and does not spill if tipped.

The cup may be manufactured inexpensively out of plastic so that it is appropriate to cost-sensitive applications, such as consumer or disposable use. Appropriate materials are: polypropylene plastic, specifically polypropylene random copolymer. Alternative transparent or semi-transparent plastics include polyethylene, polystyrene, PMMA ("Acrylic®"), polycarbonate ("Lexan®"), PET, PETG, PLA, ABS, Polymethylpentane ("TPX®"), or PVC.

Ideal, Ideally, Optimum and Preferred—Use of the words, "ideal," "ideally," "optimum," "optimum," "should" and "preferred," when used in the context of describing this invention, refer specifically a best mode for one or more embodiments for one or more applications of this invention. Such best modes are non-limiting, and may not be the best mode for all embodiments, applications, or implementation technologies, as one trained in the art will appreciate.

All examples are sample embodiments. In particular, the phrase "invention" should be interpreted under all conditions to mean, "an embodiment of this invention." Examples, scenarios, and drawings are non-limiting. The only limitations of this invention are in the claims.

All numerical ranges in the specification are non-limiting examples only. Embodiments of this invention explicitly include all combinations and sub-combinations of: all features, elements, examples and limitations of all claims, text and figures. Embodiments of this invention explicitly include devices and systems to implement any combination of all methods described in the claims, specification and drawings. Embodiments of the methods of invention explicitly include all combinations of dependent method claim steps, in any functional order. Embodiments of the methods of invention explicitly include, when referencing any device claim, a substitution thereof to any and all other device claims, including all combinations of elements in device claims.

We claim:

1. A cup comprising:
an upper chamber open at the top of the cup;
two sample-directing chambers fluidly connected to the upper chamber;
a measuring chamber fluidly connected to the sample-directing chambers;
wherein the sample-directing chambers and the measuring chamber each comprise a base and wherein the cup rests level supported by the bases, when on a horizontal surface;
wherein each sample-directing chamber is substantially in the form of a channel, comprising a sloped bottom leading into the measuring chamber;
wherein, each sample-directing chamber comprises a top open to the upper chamber;
wherein, when the cup is on a horizontal surface, a fluid placed in the upper chamber flows under gravity into at least one of the sample-directing chambers and thence to the measuring chamber;
wherein a base of the upper chamber is sloped towards one or more sample-directing chambers.

2. The cup of claim 1, wherein:
the cup comprises exactly two sample-directing chambers.

3. The cup of claim 1, wherein:
when the cup is on a horizontal surface, gravity causes fluid to flow freely from the upper chamber, via the sample-directing chambers, into the measuring chamber.

4. The cup of claim 1 further comprising:
a graduated scale adapted such that the graduated scale indicates a quantity of fluid in the cup, up to a predetermined maximum measurable fluid volume.

5. The cup of claim 1 further comprising:
a visually distinct mark at a predetermined threshold volume on the measuring chamber.

6. The cup of claim 5 wherein:
the shape of the cup is adapted such that, if the cup is resting on its side, fluid in the cup less than or equal to the threshold volume will not spill from the cup.

7. The cup of claim 1 further comprising:
a pouring spout located on a rim of the cup above the measuring chamber.

8. The cup of claim 1 comprising: a first cup and a second identical cup, wherein;
the upper chamber, each sample-directing chamber, and the measuring chamber are tapered such that the second identical cup nests inside of the first cup; and
wherein the first cup and the second identical cup are monolithic.

9. The cup of claim 1 further comprising:
an upper chamber curved lower perimeter forming a boundary between a side of the upper chamber and a base of the upper chamber;
wherein the cup is adapted such that when the cup is placed on its side on a horizontal surface that the cup rolls so that it resting on three points exactly: (i) one point of the upper chamber curved lower perimeter, and (ii) two out of three of: two bases of the sample-directing chambers and the base of the measuring chamber; and
wherein the cup is adapted such that when the cup is placed on its side on a horizontal surface that any fluid in the cup, up to a predetermined non-spilling volume, does not spill from the cup.

10. The cup of claim 1 further comprising:
an enzyme on the inside of the cup.

11. The cup of claim 1 further comprising:
a shared side of the measuring chamber that is also a portion of a side of the cup.

12. The cup of claim 11 further comprising:
a fluid volume measuring graduated scale on the shared side of the measuring chamber.

13. The cup of claim 1 wherein:
the cup is adapted such that for a first volume of fluid between a predetermined low volume and a predetermined high volume the fluid occupies a portion of the measuring chamber and a portion of both sample-directing channels, and wherein fluid levels in the cup between the predetermined low volume and a predetermined maximum measurable volume are measurable using a graduated scale on the cup.

14. The cup of claim 1 comprising: a first cup and a second identical cup, wherein;
a shape of the each sample-directing chamber and a shape of the each base of the each sample-directing chamber are adapted such that when the first cup is nested inside the second identical cup the base of the each sample-directing chamber in the first cup nests inside the each sample-directing chamber of the second identical cup;
wherein the first cup and the second identical cup are monolithic.

15. The cup of claim 1 wherein:
the entire cup fits within a circular cylinder and the inside diameter of the cylinder is the same as the outside diameter of the top of the upper chamber.

16. A method of measuring semen using the cup of claim 1 comprising the steps:
(a) placing the cup on a horizontal surface such that it is resting on its bases;

(b) placing a first quantity of semen in the upper chamber;
(c) waiting for at least a portion of the first quantity of semen to flow via the sample-directing chambers into the measuring chamber;
(d) reading the at least a portion of the first quantity of semen from a scale on the measuring chamber.

* * * * *